United States Patent [19]

Castillo et al.

[11] Patent Number: 5,336,199
[45] Date of Patent: Aug. 9, 1994

[54] MEDICAL NEEDLE AND NEEDLE SHEATH ASSEMBLY

[76] Inventors: Leo S. Castillo, 189 Sterling Glen Dr., Weterville, Ohio 43081; Gordon G. Lo, 5765 Tacoma Rd. Apt. B, Columbus, Ohio 43299

[21] Appl. No.: 150,867

[22] Filed: Nov. 12, 1993

[51] Int. Cl.$^5$ .............................................. A61M 5/32
[52] U.S. Cl. ................................... 604/198; 604/263; 128/763; 128/919
[58] Field of Search ............... 604/272, 263, 198, 192, 604/187, 110; 128/762, 764, 765, 919

[56] References Cited

U.S. PATENT DOCUMENTS

| | | | |
|---|---|---|---|
| 4,813,940 | 3/1989 | Parry | 604/198 |
| 4,897,083 | 1/1990 | Martell | 604/263 X |
| 4,915,702 | 4/1990 | Haber | 128/763 X |
| 5,139,489 | 8/1992 | Hollister | 128/763 X |

*Primary Examiner*—John D. Yasko
*Attorney, Agent, or Firm*—Thomas S. Baker, Jr.

[57] ABSTRACT

A medical needle and needle sheath assembly is provided with a sub-assembly of sheath elements that may be actuated from a retracted nested condition to an extended non-nested condition to both surround and extend beyond the medical needle element to provide protection to the medical practitioner using the assembly. A blocker element contained within the sheath sub-assembly provides additional protection against inadvertent injury to the medical practitioner when the sheath sub-assembly is in its extended condition, and further provides an obvious indication of the sheath sub-assembly retracted and extended states.

6 Claims, 4 Drawing Sheets

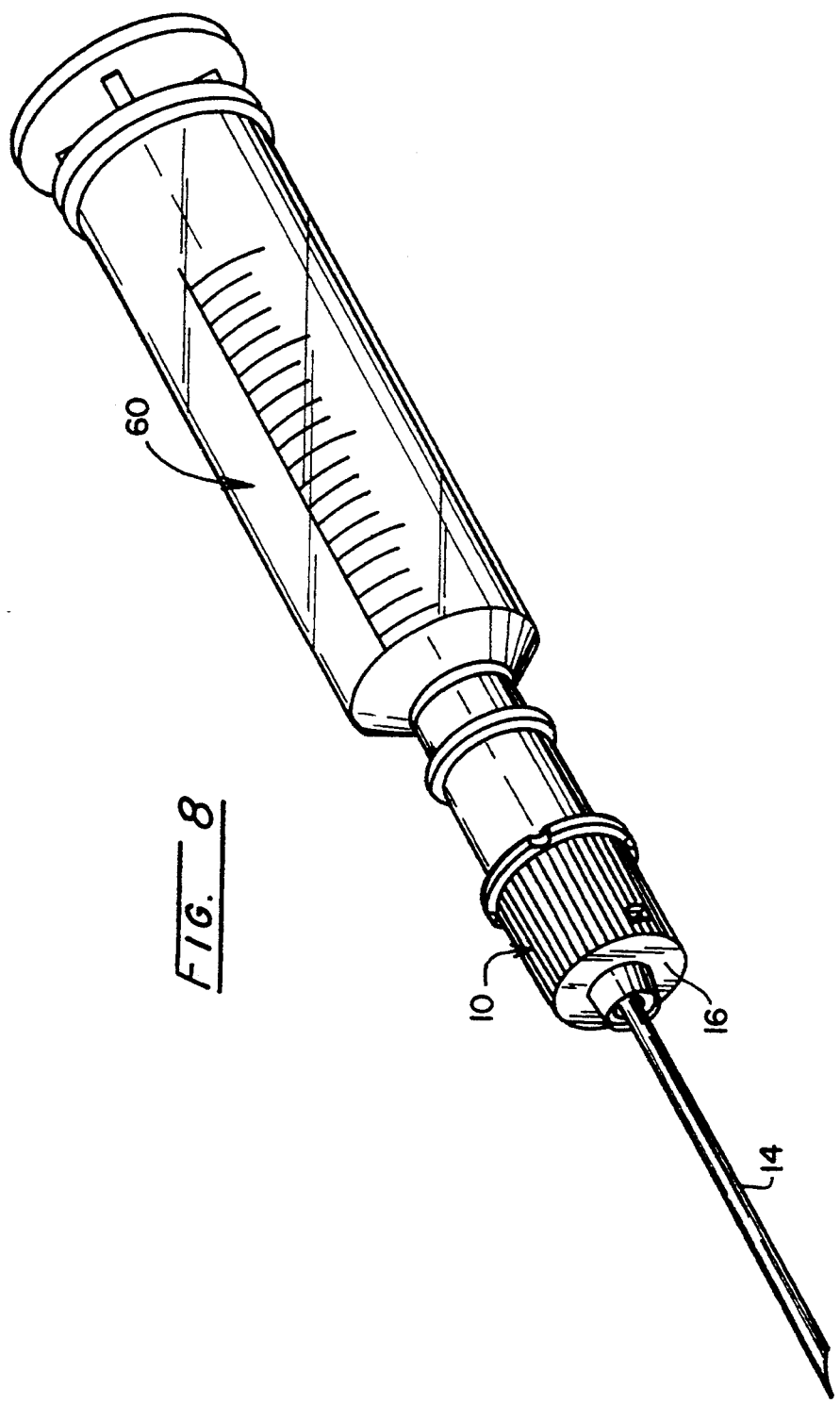

MEDICAL NEEDLE AND NEEDLE SHEATH ASSEMBLY

FIELD OF THE INVENTION

This invention relates to medical equipment generally, and particularly concerns an improved medical needle and needle sheath assembly which may be used advantageously by medical practitioners in connection with procedures for drawing patient blood samples or intravenously administering drugs to minimize the risk of practitioner injury by so-called "needlestick" and the risk of possible consequential infection in some instances.

BACKGROUND OF THE INVENTION

In recent years considerable attention has been given by designers and manufacturers of medical equipment to providing medical practitioners with improved medical devices for withdrawing patient body fluids or for injecting liquid medications or other fluids into a patient's body. Such devices typically utilize a double-ended needle in combination with an evacuated tube collector, a hypodermic syringe, supply tube, or the like. In many instances the needled devices have included some form of protective shield that surrounds the needle component to minimize the risk of accidental needlestick injury to the using practitioner due to inadvertent careless device handling. Also, the problem of providing adequate protection against inadvertent injury has received increased attention in recent years because of the prevalence of certain communicable diseases such as acquired immuno-deficiency syndrome which are known to be transmitted by contact with host human body fluids.

U.S. Pat. No. 4,752,290 issued to Schramm, for instance, discloses a needle shield having a series of raked teeth that is adapted to lock the shield around the needle in a substantially non-releasable position. Similarly, U.S. Pat. No. 4,782,841 issued in the name of Lopez teaches a needle guard member which, upon movement to a second position, is permanently locked in place by an included locking element.

U.S. Pat. No. 4,804,371 issued in the name of Vaillancourt discloses a needle sheath which is urged into its protective position around a needle point by action of a previously compressed compression spring.

U.S. Pat. No. 4,894,055 granted to Sudnak also teaches use of a spring-urged needle guard assembly as does U.S. Pat. No. 4,900,311 issued in the name of Stern et al. In the case of the latter patent the needle guard has an elliptical cross-sectional configuration and is made of a resilient material. Upon lateral compression the needle guard may be moved longitudinally between its two operative positions.

Still another patent teaching the use of a compression spring to effect movement of a protective needle housing is U.S. Pat. No. 4,929,237 issued in the name of Medway.

U.S. Pat. No. 4,947,863 granted to Haber et al. discloses a safety blood collection tube holder in which the device is provided with a plurality of successive energy absorbing and force dissipating stations at an inner cylinder. Such stations function to transform jarring impact locking forces into relatively smooth deceleration forces so as to avoid whiplash of the needle and possible splattering of that portion of the blood sample contained in the needle end.

U.S. Pat. No. 4,941,730 issued in the name of Poncy teaches a hypodermic syringe protective cap that must be rotated between first and second positions to enable the cap to be moved from an extended protective position to a retracted position exposing the syringe needle.

U.S. Pat. No. 5,030,209 granted to Wanderer et al. teaches a holder for a double-ended blood collection retractable needle with a needle retraction feature that may be readily actuated or manipulated using only one of the user's hands.

Also, U.S. Pat. 5,067,490 granted to Haber teaches a blood collection device having a double-ended needle and a protective outer sleeve. The Haber needle carrier is automatically locked into its needle-protected condition upon retraction of the outer sleeve element.

Other U.S. Patents granted by the U.S. Patent and Trademark Office and disclosing details of construction of additional medical needle devices having various guard or shield design features for protecting using medical practitioners against an accidental "needlestick" and possible consequential infection include: U.S. Pat. No. 5,067,945 issued in the name of Ryan et al., U.S. Pat. No. 5,070,884 issued in the name of Columbus et al., U.S. Pat. No. 5,070,885 issued in the name of Bonaldo, U.S. Pat. No. 5,086,780 issued in the name of Schmitt, and U.S. Reissue Pat. No. 33,585 issued in the name of Haber et al.

None of the above summarized or listed disclosures, however, provides a medical needle and needle sheath assembly which, upon extension of the included sheath or shield element, accomplishes the functions of automatically wiping the exterior of the wetted protruding needle with an absorbent material and afterwards placing a barrier in blocking alignment with the shielded needle to prevent a subsequent retraction of the in-place, extended sheath. The implementation of such functions will prevent subsequent exposure of the previously-used needle tip and possible needlestick injury to the using practitioner.

SUMMARY OF THE INVENTION

The medical needle and needle sheath assembly of this invention essentially is constructed around a core clip element into which a conventional double-ended medical needle or cannula is secured with at least one of its opposed tips exposed. Such medical needle or cannula is normally of a conventional type used for withdrawing blood or other fluids from within a human body, or for injecting liquid drugs or other fluids into the human body, often intravenously, following the piercing of human body skin with the needle. At least one collapsible needle-end sheath sub-assembly comprised of multiple nested sheath elements is mounted and secured to the clip element with the base sheath element being spring-urged from a retracted condition toward an extended condition. The needle and needle sheath assembly, when actuated, extends beyond and also around the needle exposed tip and such condition is developed following completion of the fluid-withdrawal or fluid injection procedure. Contained within the assembly is a blocker element that is retained in a spring-urged, non-blocking condition by the medical needle prior to assembly actuation, and that is moved laterally of the needle longitudinal axis to a position blocking access to the needle tip from outside the assembly when the needle sheath sub-assembly is actuated following completion of the medical procedure. The blocking element also functions in its actuated condition to indicate that the needle tip is fully protected from contact when the guard assembly is fully extended. Also, the medical needle and needle sheath assembly of this invention is provided with an internal absorbent wiper element that effectively removes any body fluid retained on the exterior surfaces of the needle to prevent aerosol following withdrawal from the patient's body as the sheath assembly is actuated and extended. Further, the assembly is also normally provided with readily removable safety caps that protect both assembly exposed medical needle ends from human contact in the pre-use sterile and packaged condition of the completed assembly.

DESCRIPTION OF THE DRAWINGS

FIG. 8 is an orthographic view of the assembly of FIG. 1 combined with a conventional hypodermic syringe.

DETAILED DESCRIPTION

Figure 1:
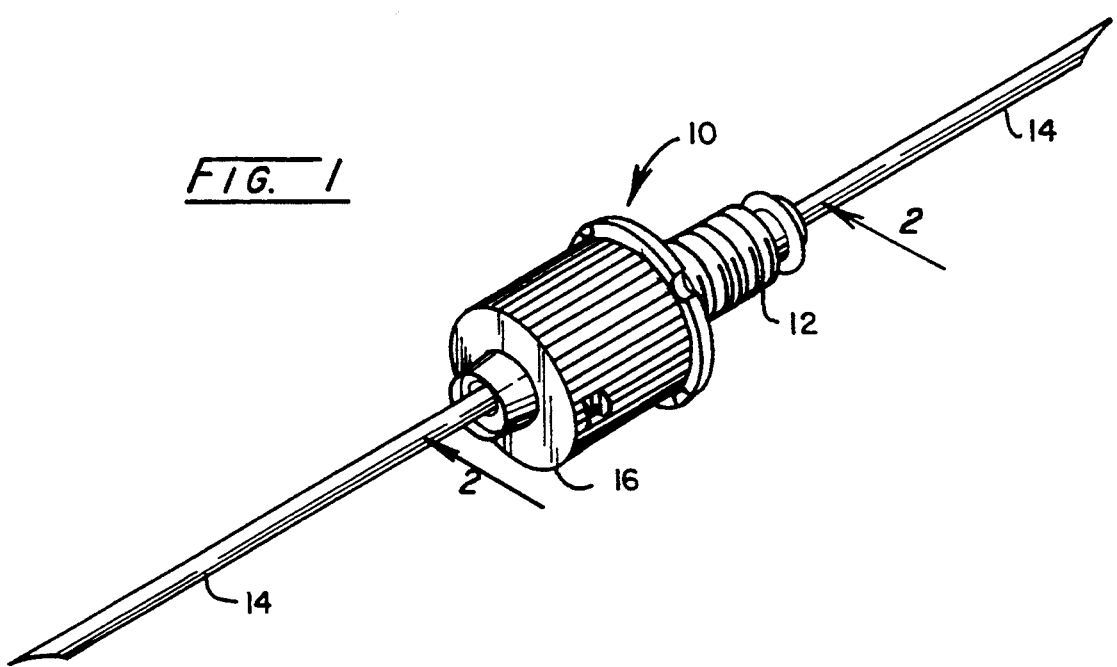
FIG. 1 is an orthographic view of a preferred embodiment of the medical needle and needle sheath assembly of this invention illustrated without those safety cap elements which are normally provided with the assembly in its subsequent sterile packaged condition.

Referring to FIG. 1, a preferred embodiment of our invention for use with a conventional air-evacuated collection tube is designated generally by the reference numeral (10) and is essentially comprised of a hub-like clip element (12) having a double-ended medical needle (14) and of a sheath sub-assembly (16) which is illustrated in FIG. 1 in its retracted or non-actuated condition. Clip element (12) is normally fabricated by molding a plastic material such as polycarbonate resin, nylon resin, or high-density polyethylene resin. In the instant embodiment, the double-end medical needle (14) is cemented in place in an inner bore (18) of clip (12) to prevent slipping or sliding of the needle (14) relative to the clip element (12) during use of assembly (10) in a medical procedure.

Figure 2:
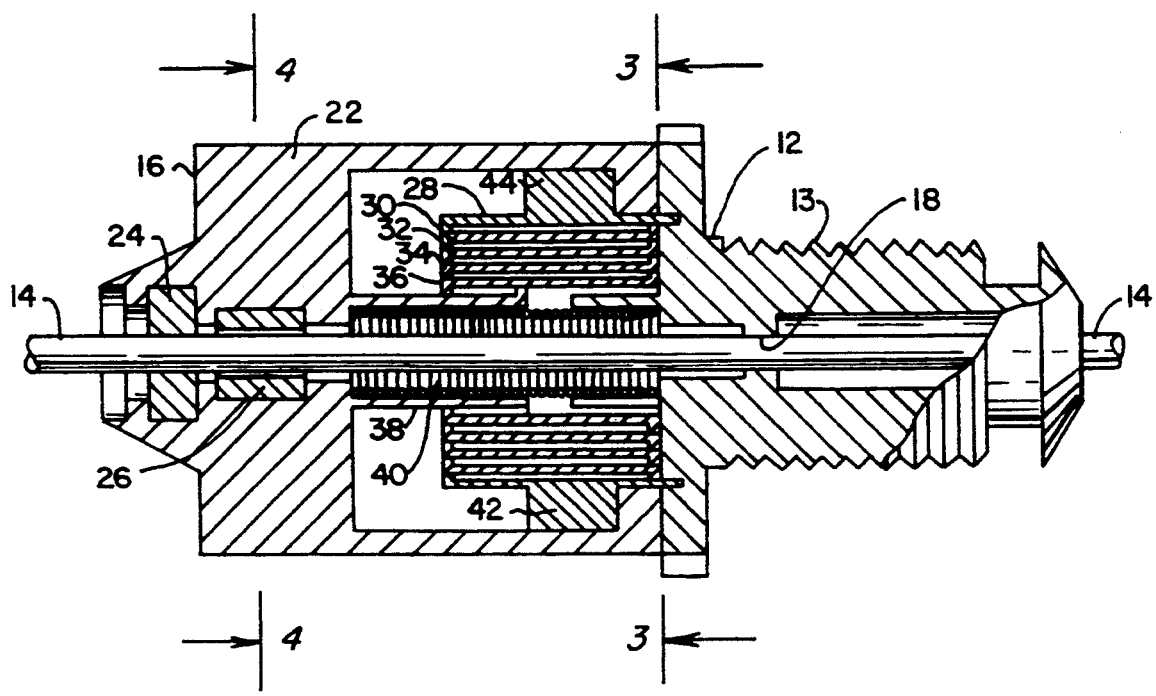
FIG. 2 is a sectional view taken along line 2—2 of FIG. 1.

Sheath assembly (16), best illustrated in detail in FIG. 2, is comprised of a molded sheath body (22) that contains in its hollow interior a wiper element (24) made of an absorbent material, a blocker member (26), a group of nested sheath elements (28, 30, 32, 34, 36, and 38), and a compression spring member (40). Each of the nested sheath elements (28 through 36) is provided at its leftmost extreme with a radially, inwardly-extending lip that is engaged by a respective radially, outwardly-extending lip provided at the rightmost extreme of each of sheath elements (30 through 38) when assembly (16) is actuated. Such actuation occurs by the rotation of sheath body (22) relative to needle clip (12) to cause an extension of the retracted assembly by the action of compression spring (40). Outermost sheath element (28) is bonded at its rightmost extreme to an annular groove provided in needle clip (12). Innermost sheath element (38) is bonded at its leftmost extreme to an annular groove provided in sheath body (22) to facilitate nesting assembly of elements (28 through 38).

Figure 3:
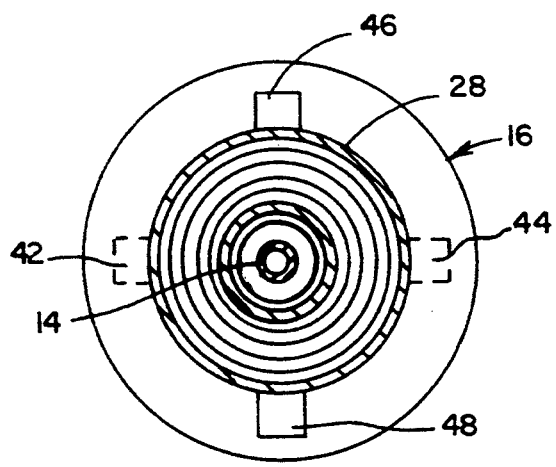
FIG. 3 is a sectional view taken along line 3—3 of FIG. 2.

Assembly (10) is provided with means for latching sheath body (22) to needle clip (12) to retain compression spring (40) in its compressed condition and to retain sheath elements (28 through 38) in their nested condition prior to the release of spring (40) and consequent extension of sub-assembly (16). That latching action is essentially obtained by the provision of a pair of diametrically-opposed wing elements (42 and 44) that are inserted into the interior of sheath body through a pair of diametrically-opposed radial slots (46 and 48) provided in the rightmost annular wall portion of sheath body (22). See FIG. 3.

Figure 4:
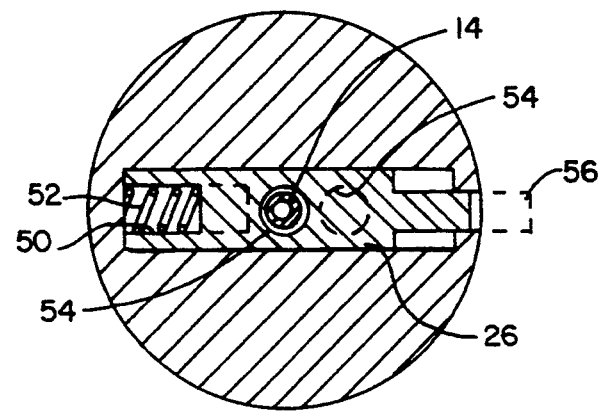
FIG. 4 is a sectional view taken along line 4—4 of FIG. 2.
Figure 5:
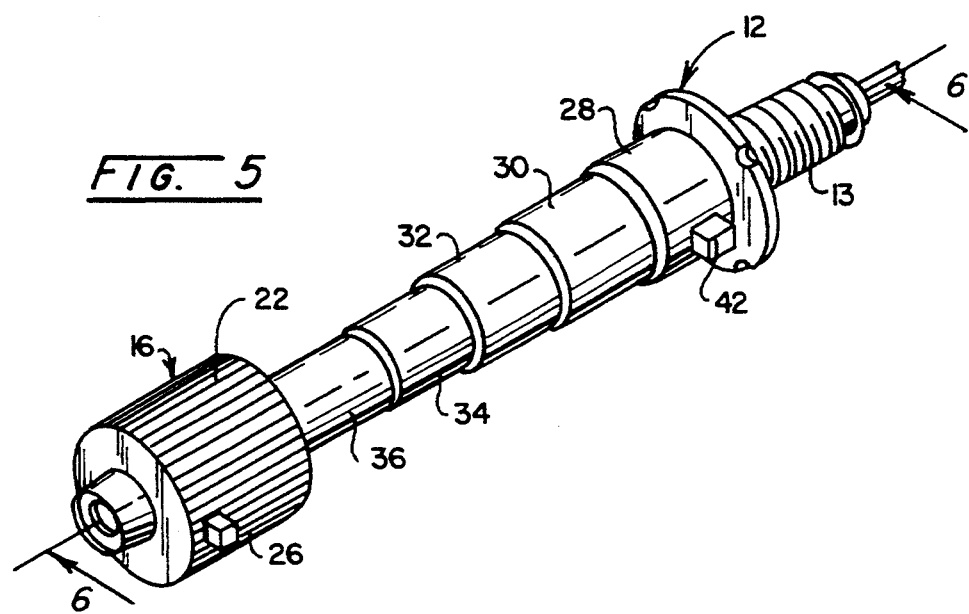
FIG. 5 is an orthographic view of the medical needle and needle sheath assembly of FIG. 1 but with the included sheath elements being in an actuated and extended condition.
Figure 6:
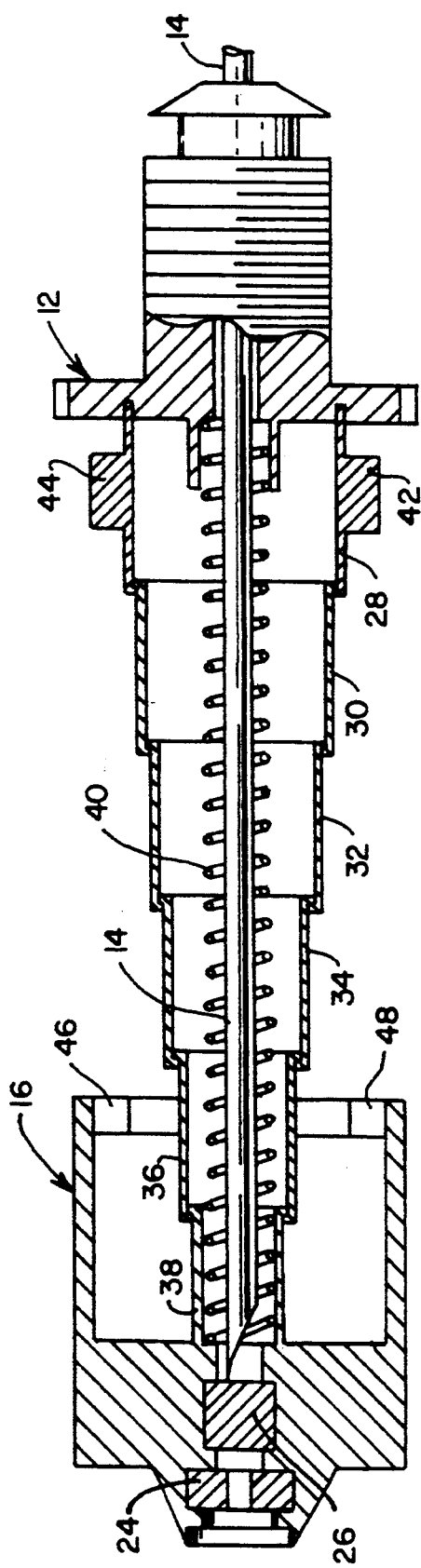
FIG. 6 is a sectional view taken along line 6—6 of FIG. 5.

Details regarding the blocker element (26) contained within sheath body (22) are best developed by reference to FIG. 4 of the drawings. Element (26), which preferably is molded of the same material that sheath body (22) and its contained nested sheath elements (28 through 38) are molded, has a recess (50) into which a small compression spring (52) is inserted for compression during the assembly process. Blocker element (26) also contains an opening (54) through which needle (14) is passed during sheath assembly. Also, blocker element (26) is provided with an indicator portion (56) at its rightmost extreme. In the sheath retracted condition, needle (14), because it passes completely through blocker element (26), prevents spring (52) from moving blocker element (26) from its recessed condition to its extended position indicating that the adjacent tip of needle (14) is completely blocked from accidental or even intentional contact by a using practitioner. The spring action of extending sheath sub-assembly (16) from its retracted condition causes needle (14) to be withdrawn from opening (54) in blocker element (26) thus permitting compressed spring member (52) to move element (26) to an extended position whereat its indicator portion (56) is projected outside the exterior cylindrical surface of sheath body (22).

Also, the embodiment of our invention illustrated in FIGS. 1 through 6 is provided with an external thread (13) on its boss portion of clip element (12). Such threaded boss is provided for the purpose of cooperation with a corresponding internal thread as provided in at least one form of commercially-available holder. FIG. 8 illustrates a commercially-available hypodermic syringe (60) combined with another version of the needle and needle sheath assembly (10) in a condition ready for use.

Figure 7:
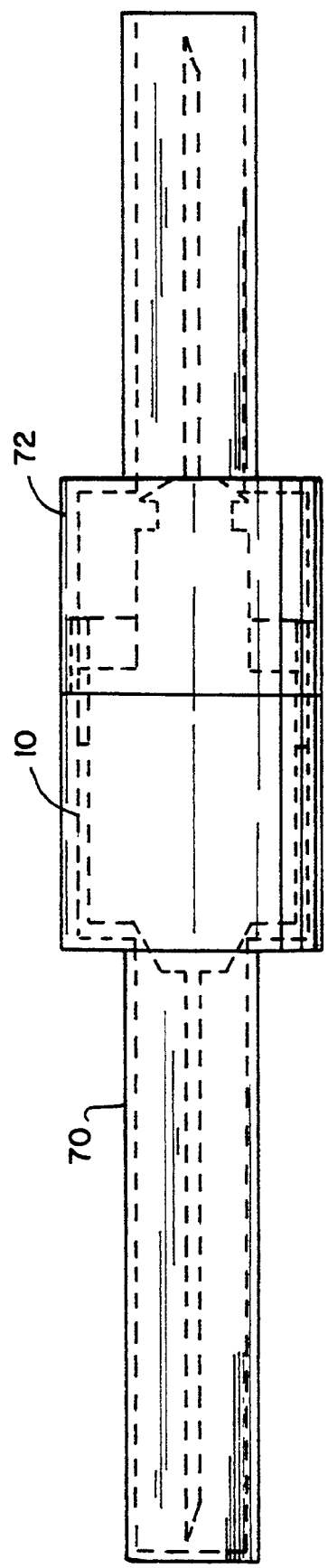
FIG. 7 is an elevational view of the assembly of FIG. 1 with included safety cap elements to minimize possible inadvertent injury during pre-use assembly handling.

FIG. 7 illustrates the use of safety cap elements (70 and 72) in combination with assembly (10). Such hollow safety cap elements are normally fabricated by molding as in the manner of fabricating sheath body (22). Although not detailed in the drawings, it is preferred that such safety caps cooperate with and be secured to the flange portion of needle clip elements (12) in a readily detachable manner. FIG. 7 essentially discloses the needle and needle sheath assembly (10) of our invention in the sterile packaged condition in which it is normally furnished to a using practitioner.

Other materials, component shapes, and component sizes may be utilized in the practice of this invention.

We claim our invention as follows:

1. In a medical needle and needle sheath assembly, in combination;
    a core clip element supporting a double-ended medical needle with exposed tips;
    a sheath sub-assembly attached to said clip element in surrounding relation to a portion of said double-ended medical needle and having a retracted condition and an extended condition;
    a multiplicity of cooperating sheath elements nested with respect to each other in said sub-assembly retracted condition and non-nested with respect to each other in said sub-assembly extended condition;
    compression spring means urging said sheath sub-assembly to said sub-assembly extended condition when compressed; and
    releasable latch means securing said sheath sub-assembly to said clip element in said sheath sub-assembly retracted condition, said latch means being released by rotation relative to said clip element to cause said sheath sub-assembly to assume said sub-assembly extended condition by the action of said compression spring means.

2. The invention defined by claim 1 and further comprised of a wiper element contained within said sheath sub-assembly in contacting relation to said medical needle, said wiper element being an absorbent material which wipes an exterior surface of said medical needle when said latch means is released and said sheath sub-assembly is moved by said compression spring means to assume said sheath sub-assembly extended condition.

3. The invention defined by claim 1 and further comprised of a spring-urged blocker element within said sheath sub-assembly and movable laterally relative to the longitudinal axis of said medical needle between a retracted condition and an extended condition, said blocker element being retained in its retracted condition by said medical needle when said sheath sub-assembly is in said sheath sub-assembly retracted condition.

4. The invention defined by claim 3 wherein said spring-urged blocker element includes an indicator portion, said indicator portion being contained interiorly of said sheath sub-assembly when said sheath sub-assembly assumes is in said sheath sub-assembly retracted condition and being projected exteriorly of said sheath sub-assembly when said sheath sub-assembly is in said sheath sub-assembly extended condition.

5. A medical needle and needle sheath assembly comprising;
    a clip means supporting a double-ended medical needle with exposed needle tips;
    at least one needle sheath attached to said clip means in surrounding relation to said medical needle and having a retracted condition prior to actuation and an extended condition subsequent to actuation;
    compression spring means urging said needle sheath to said sheath extended condition when compressed;
    latch means releasably securing said needle sheath to said clip means; and
    spring-urged blocker means movable laterally relative to the longitudinal axis of said medical needle sand having a retracted condition and an extended condition, said blocker means being retained in its retracted condition by said medical needle when said needle sheath is in said needle sheath retracted condition and moved to its extended condition by said compression spring means when said needle sheath is in said needle sheath extended condition due to the action of said compression spring means.

6. The invention defined by claim 5 wherein said blocker means has an indicator portion, said blocker means indicator portion having a first position interiorly of said needle sheath when said needle sheath is in said needle sheath retracted condition and a second position exteriorly of said needle sheath when said needle sheath is in said needle sheath extended condition.

* * * * *